US012642675B2

(12) United States Patent
Horton et al.

(10) Patent No.: US 12,642,675 B2
(45) Date of Patent: Jun. 2, 2026

(54) STENT AND METHOD FOR USE THEREOF

(71) Applicants:Joseph Horton, Birmingham, AL (US);
Marcelino Bowker Gorospe, Redwood
City, CA (US); Mohit Dhoriya, Bethel
Park (IN)

(72) Inventors: Joseph Horton, Birmingham, AL (US);
Marcelino Bowker Gorospe, Redwood
City, CA (US); Mohit Dhoriya, Bethel
Park (IN)

(73) Assignee: FLOW DIRECTORS, LLC,
Birmingham, AL (US)

( * ) Notice: Subject to any disclaimer, the term of this
patent is extended or adjusted under 35
U.S.C. 154(b) by 27 days.

(21) Appl. No.: 18/409,140

(22) Filed: Jan. 10, 2024

(65) Prior Publication Data

US 2024/0225655 A1     Jul. 11, 2024

Related U.S. Application Data

(60) Provisional application No. 63/438,169, filed on Jan.
10, 2023.

(51) Int. Cl.
A61F 2/82          (2013.01)
A61B 17/12         (2006.01)
A61F 2/90          (2013.01)

(52) U.S. Cl.
CPC .......... A61F 2/90 (2013.01); A61B 17/12036
(2013.01); A61B 17/1214 (2013.01); **A61B
17/12109 (2013.01); A61F 2002/823**
(2013.01); A61F 2250/0039 (2013.01)

(58) Field of Classification Search
CPC ........ A61B 17/12109; A61B 17/12036; A61B
17/1214; A61B 17/12145; A61F
2002/823; A61F 2/90; A61F 2/91; A61F
2/92; A61F 2250/0039
See application file for complete search history.

(56) References Cited

U.S. PATENT DOCUMENTS

| | | | |
|---|---|---|---|
| 9,095,420 B2 | 8/2015 | Malek | |
| 9,211,202 B2 | 12/2015 | Strother et al. | |
| 2004/0039435 A1* | 2/2004 | Hancock | .......... A61B 17/12022 |
| | | | 623/1.2 |

(Continued)

FOREIGN PATENT DOCUMENTS

| | | | |
|---|---|---|---|
| WO | WO2006052322 | 5/2006 | |
| WO | WO-2019059949 A2 * | 3/2019 | ............. A61F 2/915 |

OTHER PUBLICATIONS

A Novel Fully Covered Double-Bump Stent for Staple Line Leaks
After Bariatric Surgery: A Retrospective Analysis, Boerlage et al.,
Jan. 17, 2018, Surgical Endoscopy, vol. 32, pp. 3174-3180.

(Continued)

*Primary Examiner* — Katherine M Shi
*Assistant Examiner* — Erin L Colello

(57)          ABSTRACT

A stent and methods for use of the stent are provided. The
stent is positionable in a blood vessel adjacent an opening to
an aneurysm. The stent is configured to deflect portions of
blood flow away from the opening to the aneurysm to
decrease the amount of blood flow entering the aneurysm
and decrease the rate at which blood floor enters the aneu-
rysm, and/or increase the amount and control the direction
of the blood flow out of the aneurysm.

19 Claims, 12 Drawing Sheets
(6 of 12 Drawing Sheet(s) Filed in Color)

DIRECTION OF BLOOD FLOW

(56)                    References Cited

U.S. PATENT DOCUMENTS

2010/0106180 A1 *   4/2010   Strother .................... A61F 2/82
                                                        606/200
2018/0368965 A1 *  12/2018   Janardhan ............... A61M 1/84
2021/0007868 A1     1/2021   Molaei et al.

OTHER PUBLICATIONS

Flow Diversion to Treat Aneurysms: The Free Segment of Stent, Darsaut et al., Jul. 10, 2012, Journey of Neurointerventional Surgery, vol. 5, pp. 452-457.
Y-Stent-Assisted Coil Embolization of Wide-Neck Intracranial Aneurysms: A Single Center Experience, Akgul et al., Mar. 1, 2011, Interventional Neuroradiology, vol. 17, pp. 36-48.

* cited by examiner

DIRECTION OF BLOOD FLOW

DIRECTION OF BLOOD FLOW

DIRECTION OF BLOOD FLOW

STENT AND METHOD FOR USE THEREOF

The present application claims benefit of Provisional Application No. 63/438,169, filed Jan. 10, 2023, which is hereby incorporated by reference herein.

FIELD

The present technology generally relates to a stent and methods for use thereof in which the stent is positionable in a blood vessel adjacent an opening to an aneurysm, and is configured to deflect portions of blood flow away from the opening to the aneurysm to decrease the amount of blood flow entering the aneurysm, and/or increase and control the direction of the blood flow out of the aneurysm.

BACKGROUND

Aneurysms are outward bulges or bubbles formed in a wall of a blood vessel that are caused by deficiencies in the wall of the blood vessel. Such deficiencies can be caused by weaknesses in the walls of the blood vessels, which, under pressure of blood flow flowing therethrough causes the outward bulges or bubbles forming the aneurysms. The aneurysms form openings in the walls of the blood vessels, and the blood flow from the blood vessels can enter interiors of the aneurysms through the openings. The blood flow into the interiors of the aneurysms via the aneurysm openings can cause rupture thereof. Conventional stents have been used to occlude the aneurysm openings in the blood vessel to prevent such rupture. These conventional stents are typically made of relatively high density materials that block the flow of blood into the aneurysms via such occlusion of the aneurysm openings. However, the occlusion afforded by use of such conventional stents can lead to undesirable delayed hemorrhaging. Therefore, there is a need for an improved stent that can be implanted in blood vessels or portions thereof that, rather than occluding aneurysm openings can at the very least maximize the blood flow BF away from the aneurysms by decreasing the amount of the blood flow entering the aneurysms, and decreasing the rate at which the blood flow enters the aneurysms.

SUMMARY

The techniques of this disclosure generally relate to a stent and methods for use thereof in which the stent is implantation in a blood vessel adjacent an opening to an aneurysm to reduce negative effects of blood flow flowing through the blood vessel into the aneurysm.

In one aspect, the present disclosure provides a stent for implantation in a blood vessel adjacent an opening to an aneurysm, the stent including a tubular portion having a first end, an opposite second end, a length extending between the first end and the second end, a mid-longitudinal axis extending through the first end and the second end, a first opening at the first end, a second opening at the second end, and an interior passageway extending through the tubular portion between the first opening and the second opening; the stent having at least a first waist and a second waist formed as narrowed areas in the tubular portion, the first waist and the second waist being positioned adjacent to another, the second waist being closer to the second end than the first waist, and the first waist and the second waist each having minimum outer diameters smaller than maximum outer diameters of the tubular portion adjacent the first waist and the second waist in corresponding planes extending therethrough that are perpendicular the mid-longitudinal axis; where the stent is positionable in the blood vessel with the first waist and the second waist positioned upstream of the opening to the aneurysm, the first waist and the second waist serve in deflecting flow of blood through the blood vessel away from the opening to the aneurysm to at least decrease rates of flow of blood entering the aneurysm; and where, when the first waist and the second waist are positioned upstream of the opening to the aneurysm, the tubular portion is uninterrupted adjacent the opening to the aneurysm and immediately downstream of the opening to the aneurysm by additional waists.

In another aspect, the present disclosure provides a method for optimal placement of a stent in a blood vessel adjacent an opening to an aneurysm and using the stent to reduce deleterious effects of blood flow on the aneurysm, the method including providing the stent having a tubular shape, a first end, an opposite second end, a length extending between the first end and the second end, a mid-longitudinal axis extending through the first end and the second end, a first opening at the first end, a second opening at the second end, and a passageway extending between the first opening and the second opening; implanting the stent in the blood vessel, positioning a first waist and a second waist formed in the stent upstream of the opening of the aneurysm, the first waist and the second waist being formed as narrowed areas in the tubular shape, the first waist and the second waist being positioned adjacent to another, the second waist being closer to the second end than the first waist, and the first waist and the second waist each having minimum outer diameters smaller than maximum outer diameters of the tubular shape adjacent the first waist and the second waist in corresponding planes extending therethrough that are perpendicular the mid-longitudinal axis; and directing the flow of blood through the blood vessel away from the opening to the aneurysm to at least decrease rates of flow of blood entering the aneurysm via interaction with the flow of blood with the first waist and the second waist; where, when the first waist and the second waist are positioned upstream of the opening to the aneurysm, the tubular shape is uninterrupted adjacent the opening to the aneurysm and immediately downstream of the opening to the aneurysm by additional waists.

In yet another aspect, the present disclosure provides a method for optimal placement of a stent in a blood vessel adjacent an opening to an aneurysm and using the stent to reduce deleterious effects of blood flow on the aneurysm, the method including implanting the stent in the blood vessel by positioning a first waist and a second waist formed in the stent upstream of the opening of the aneurysm, the stent having a tubular shape, the first waist and the second waist being formed as narrowed areas in the tubular shape, the first waist and the second waist being positioned adjacent to another, and the first waist and the second waist each having minimum outer diameters smaller than maximum outer diameters of the tubular shape adjacent the first waist and the second waist in corresponding planes extending therethrough that are perpendicular to a mid-longitudinal axis of the stent; and directing the flow of blood through the blood vessel away from the opening to the aneurysm to at least decrease rates of flow of blood entering the aneurysm via interaction with the flow of blood with the first waist and the second waist; where, when the first waist and the second waist are positioned upstream of the opening to the aneurysm, the tubular shape is uninterrupted adjacent the opening to the aneurysm and immediately downstream of the opening to the aneurysm by additional waists.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

The techniques of this disclosure generally relate to a stent and a method for using the stent.

DETAILED DESCRIPTION

Figure 1A:
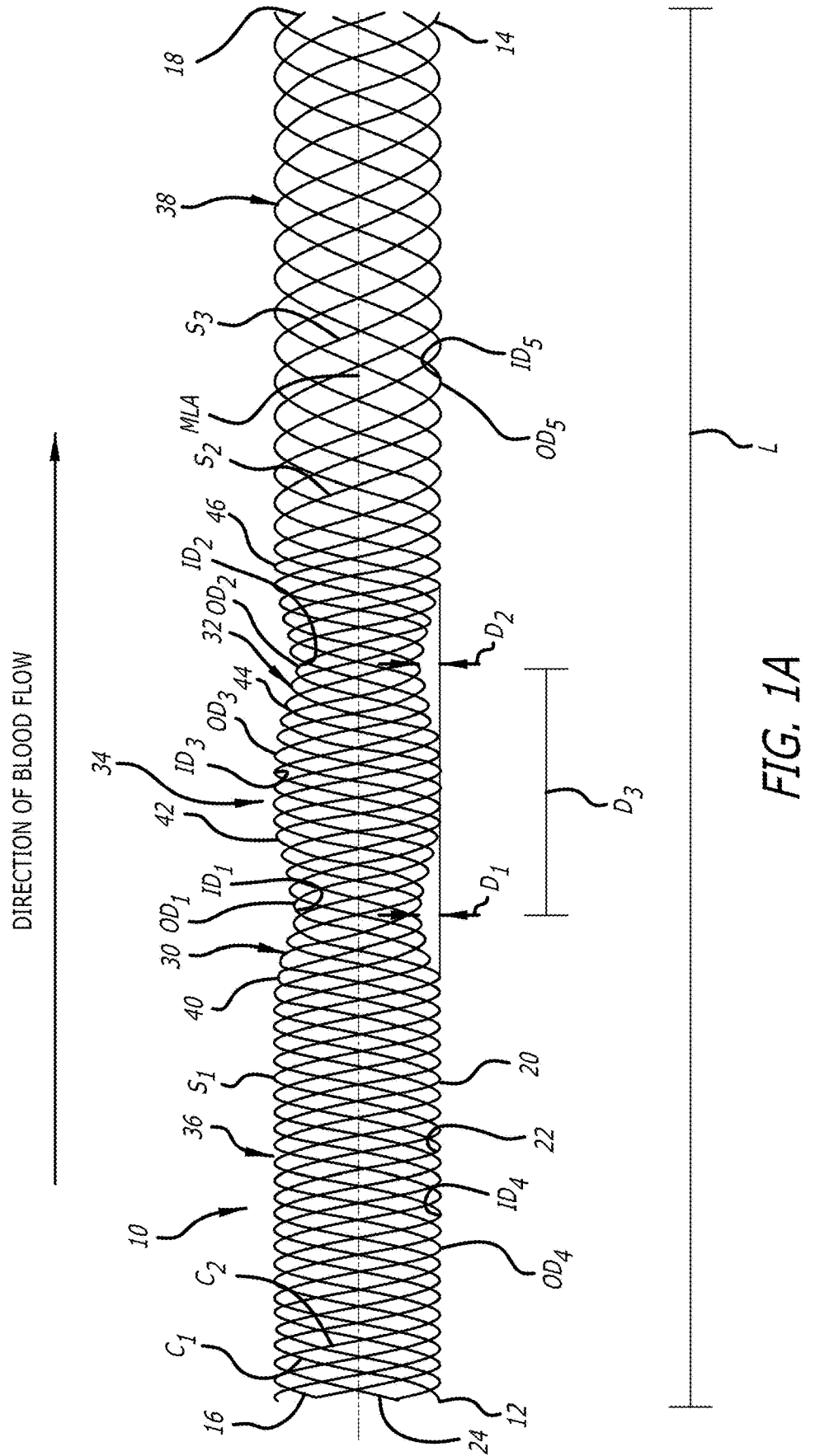
FIG. 1A is a side, elevational view of a stent in accordance with an embodiment of the present disclosure.
Figure 1B:
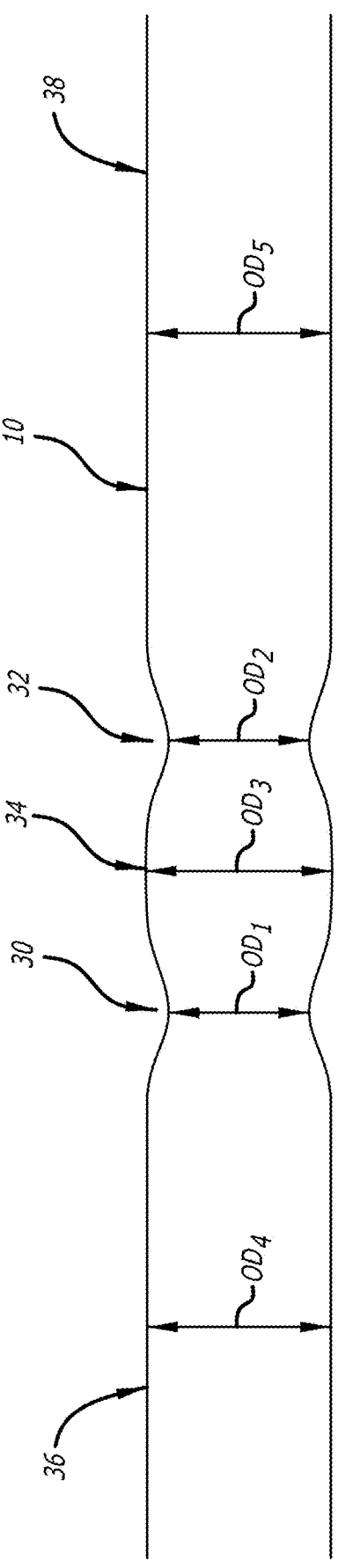
FIG. 1B is a side, elevational representation of an outer locus of the stent of FIG. 1A.
Figure 2:
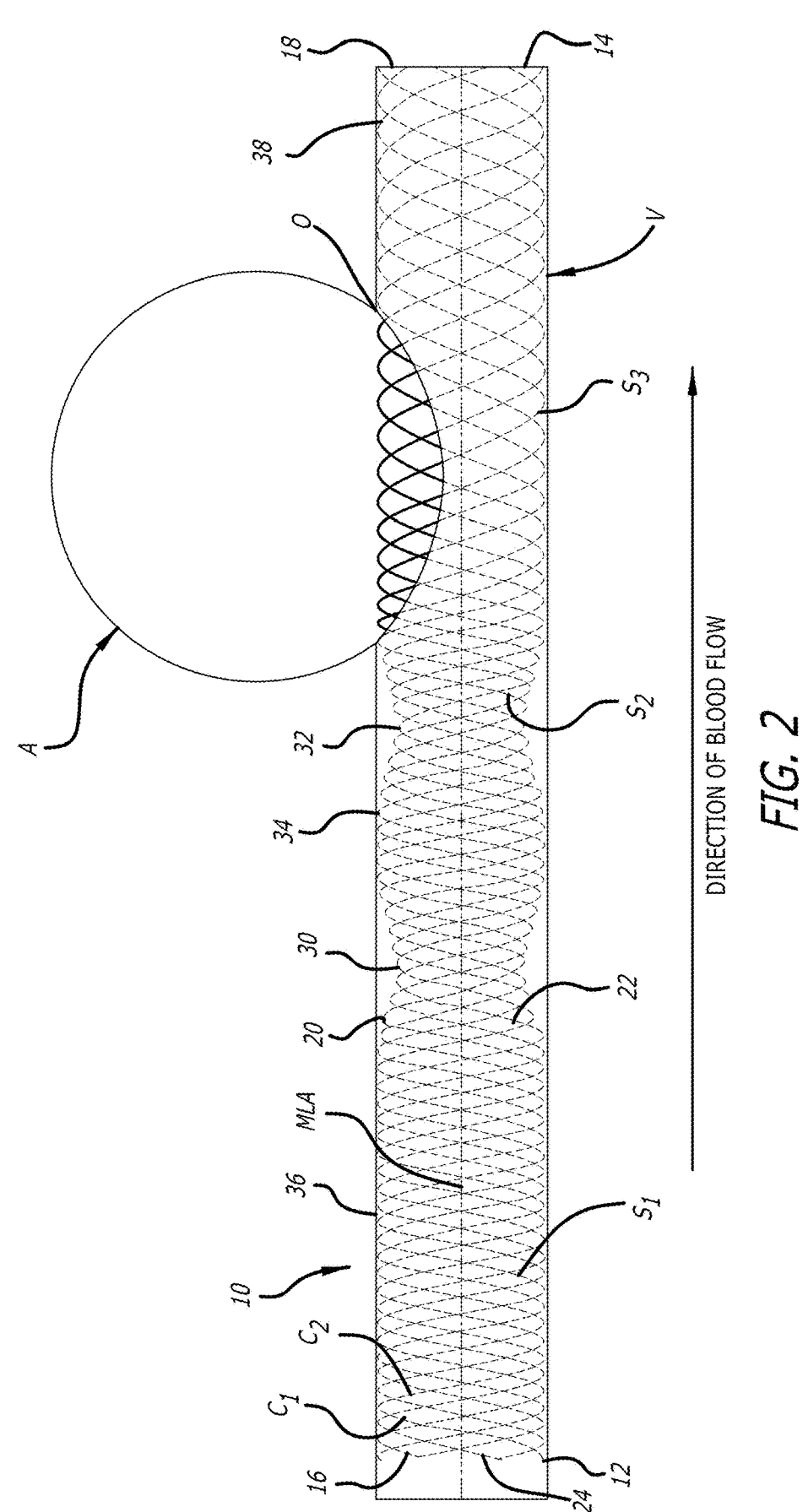
FIG. 2 is a side, elevational view of the stent of FIG. 1A positioned in a blood vessel adjacent an opening to an aneurysm, in which the blood vessel and the aneurysm are semi-transparent to afford depiction of the stent.
Figure 3:
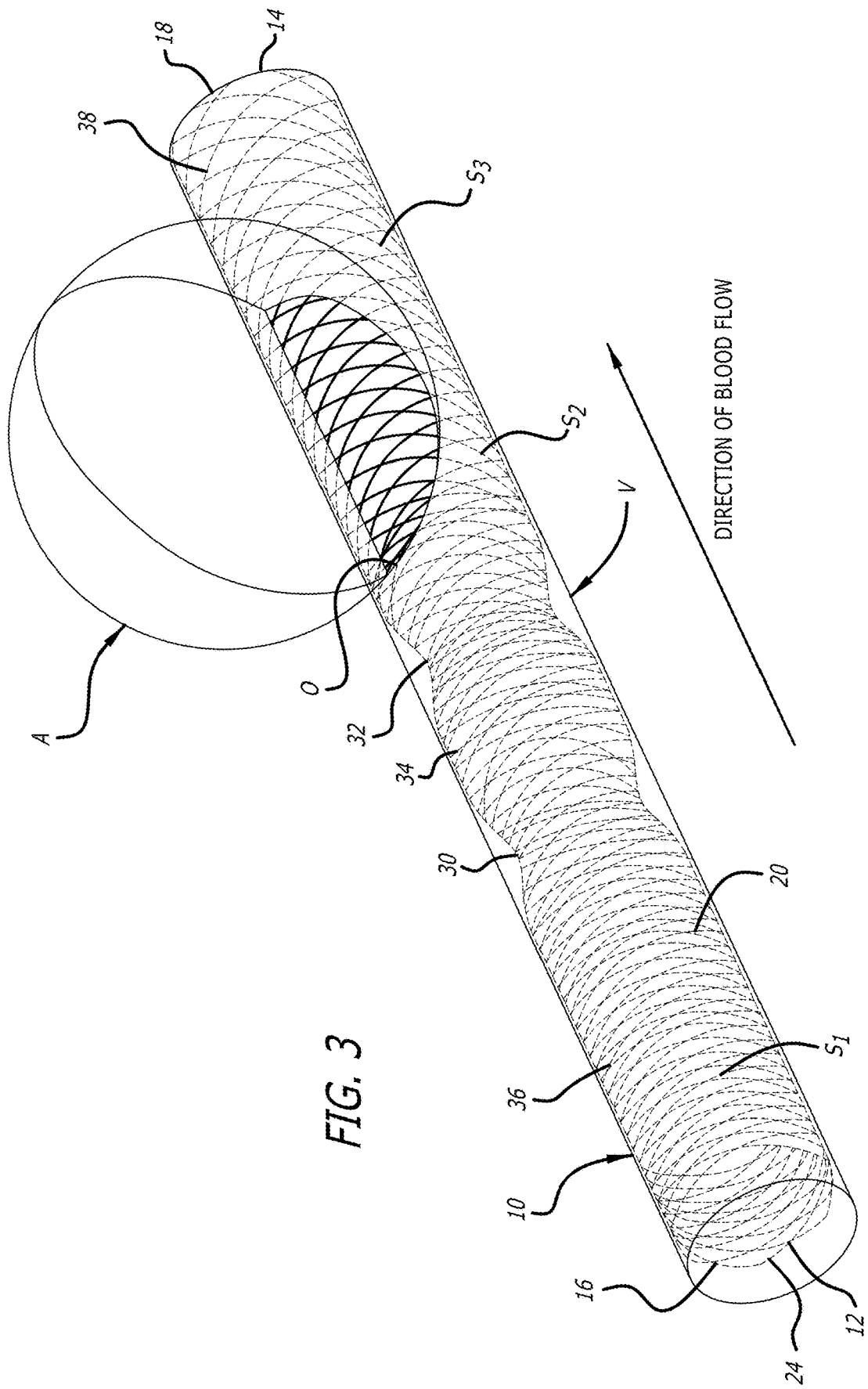
FIG. 3 is a top, side, perspective view of the stent of FIG. 1A positioned in a blood vessel adjacent an opening to an aneurysm, in which the blood vessel and the aneurysm are semi-transparent to afford depiction of the stent.
Figure 4:
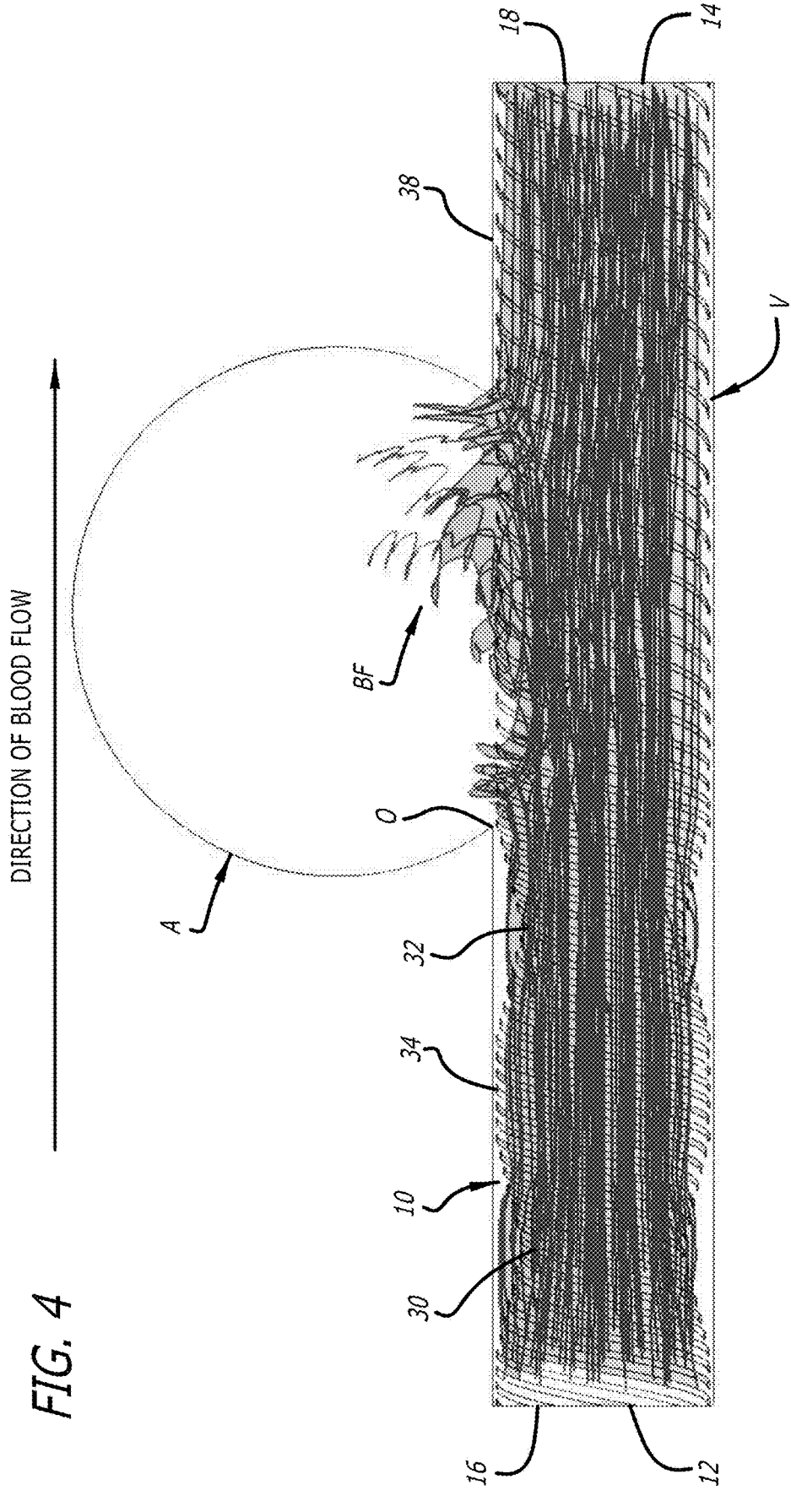
FIG. 4 depicts output of a computer model modeling blood flow flowing through a blood vessel and an aneurysm as effected by placement of the stent of FIG. 1A.

An embodiment of a stent 10 according to the present disclosure is depicted in FIGS. 1A-4, and the stent 10 can be used in association with an aneurysm A (FIGS. 2-4) for decreasing deleterious effects thereof. An outer locus (or virtual shape envelope) of the stent 10 is depicted in FIG. 1B. As depicted in FIGS. 2-4, the aneurysm A is formed in a blood vessel V, and blood flow BF passing through the blood vessel V enters the aneurysm A via an opening (or entrance) O in a wall of the blood vessel V. The stent 10 and the methods for using the stent 10, according to the present disclosure, afford implantation the stent 10, as depicted in FIGS. 2-4, in the blood vessel V adjacent the opening O to the aneurysm A to reduce negative effects of blood flow flowing through the blood vessel V on the aneurysm A. By reducing such negative effects, the stent 10 and the methods for using the stent 10 can reduce the potential for rupture of the aneurysm A.

As discussed below, the stent 10 is configured and placed relative the opening O to affect the amounts of the blood flow BF directed toward and away from the opening O of the aneurysm A, and simultaneously, control the amounts and the direction of the blood flow BF into and/or out of the aneurysm A. In particular, as depicted in FIGS. 2-4, during implantation of the stent 10, portions of the stent 10 can be positioned in the blood vessel V adjacent to the opening O, and the configurations and the placement of the stent 10 relative the opening O and the interaction of the blood flow BP therewith serves to deflect portions of the blood flow BF away from the aneurysm opening O to (A) decrease the amount of blood flow BF entering the aneurysm A and (B) decrease the rate at which blood flood enters the aneurysm A, and/or (C) increase the amount and control the direction of the blood flow BF out of the aneurysm A.

The stent 10 can have a flexible configuration formed at least in part by a wire strand or wire strands of material wound in coiled or substantially-coiled configurations. For example, the stent 10 can be made of at least one (1) and preferably two (2) or more coils formed by the wire strand or the wire strands of material. In some instances, the stent 10 can be made of two (2) to fifty (50) or even more coils. The coils can be interwoven, braided, and/or interleaved with one another to form a tubular configuration. To illustrate, the stent 10, as depicted in FIGS. 1A and 2, can be formed from a first coil $C_1$ and a second coil $C_2$ interwoven, braided, and/or interleaved with one another to form the tubular configuration with one of the first coil $C_1$ and the second coil $C_2$ being wound in a left-hand direction, and the other of the first coil $C_1$ and the second coil $C_2$ being wound in an opposite right-hand direction. Windings of the strands of material forming the first coil $C_1$ and the second coil $C_2$ of the stent 10 can be helical or substantially-helical. And the strands of material forming the first coil $C_1$ and the second coil $C_2$ of the stent 10 can be metallic, semi-metallic, or non-metallic cords, threads, twines, and/or wires. In addition to or alternatively, the stent 10 can be formed via removal of material from a tubular or semi-tubular structure of metallic, semi-metallic, or non-metallic materials. To illustrate, laser-cutting, etching, and/or other material removal techniques can be used to cutaway portions of the tubular structure to create results similar to the tubular configuration formed by the interweaving, braiding, and/or interleaving of two (2) or more coils such as the first coil $C_1$ and the second coil $C_2$.

As depicted in FIG. 1A, the stent 10 has a first end 12, an opposite second end 14, a length L extending between the first end 12 and the second end 14, and a mid-longitudinal axis MLA extending through the stent 10. And, as depicted in FIG. 1A, the stent 10 includes a first opening 16 at the first end 12, a second opening 18 at the second end 14, exterior-facing surfaces 20 on the exterior of the stent 10, interior-facing surfaces 22 on the interior of the stent 10, and an interior passage 24 extending through the stent 10 between the first opening 16 and the second opening 18.

The stent 10 can preferably include two (2) or more waist portions that are reduced-diameter portions of the stent 10 that look like narrowed, pinched, or circumferentially-contracted areas that together resemble generally wave-like shapes along the stent 10, and these waist portions can be used to advantageously maximize the blood flow BF away from and out of the aneurysm A by (A) decreasing the amount of the blood flow BF entering the aneurysm A and (B) decreasing the rate at which the blood flow enters the aneurysm A, and/or (C) increasing the amount and control-ling the direction of the blood flow BF out of the aneurysm A. For example, the stent 10, as depicted in FIGS. 1A-4, can include a first waist portion 30 and a second waist portion 32 positioned adjacent to one another. The first waist portion 30 and the second waist portion 32, as depicted in FIG. 1A, are reduced-diameter portions of the stent 10 that look like narrowed, pinched, or circumferentially-contracted areas that together resemble generally wave-like shapes along the stent 10. As depicted in FIGS. 1A-4, the stent 10 also includes an intermediate portion 34 positioned between the first waist portion 30 and the second waist portion 32, a tubular upstream portion 36 positioned upstream of the first waist portion 30 and the second waist portion 32, and a downstream tubular portion 38 positioned downstream of the first waist portion 30 and the second waist portion 32.

As depicted in FIGS. 1A and 2, pitches of the helical windings of the first coil $C_1$ and the second coil $C_2$ can be uniform or varied along the length of the stent 10. As depicted in FIG. 1A, the pitches and arrangement of the first coil $C_1$ and the second coil $C_2$ at the first waist portion 30, the second waist portion 32, the intermediate portion 34, the upstream portion 36, and the downstream portion 38 create first spaces $S_1$, second spaces $S_2$, and third spaces $S_3$ therealong. Depending on whether the pitches of the helical windings of the first coil $C_1$ and the second coil $C_2$ are uniform or varied, the shapes of the first spaces $S_1$, the second spaces $S_2$, and the third spaces $S_3$ can correspondingly be uniform or varied.

Furthermore, given that the first coil $C_1$ and the second coil $C_2$ are helical or substantially-helical, the tubular configuration of the stent 10 can have circular or substantially circular cross-sections in first planes perpendicular to the mid-longitudinal axis MLA. As depicted in FIG. 1A, the first waist portion 30 and the second waist portion 32 have minimum first outer and inner diameters $OD_1$ and $ID_1$, and minimum second outer and inner diameters $OD_2$ and $ID_2$, respectively. Furthermore, the intermediate portion 34 has maximum third outer and inner diameters $OD_3$ and $ID_3$, the upstream portion 36 has maximum fourth outer and inner diameters $OD_4$ and $ID_4$, and the downstream portion 38 has maximum fifth outer and inner diameters $OD_5$ and $ID_5$.

Prior to implantation of the stent 10 and in second planes extending through and along the mid-longitudinal MLA and moving from the first end 12 to the second end 14, an outer locus (FIG. 1B) and an inner locus at the upstream portion 36 are constant or at least substantially constant at the maximum fourth outer and inner fourth diameters $OD_4$ and $ID_4$, respectively; an outer locus (FIG. 1B) and an inner locus at the first waist portion 30 narrow from the upstream portion 36 to the minimum first outer and inner diameter $OD_1$ and $ID_1$, respectively, and expand therefrom to the intermediate portion 34; an outer locus (FIG. 1B) and an inner locus of the intermediate portion 34 are constant or at least substantially constant at the maximum third outer and inner diameters $ID_3$ and $OD_3$, respectively; an outer locus (FIG. 1B) and an inner locus of the second waist portion 32 narrow from the intermediate portion 34 to the minimum second outer and inner diameter $ID_2$ and $OD_2$, respectively, and expand therefrom to the downstream portion 38; and an outer locus (FIG. 1B) and an inner locus of the downstream portion 38 are constant or at least substantially constant at the maximum fifth outer and inner diameters $ID_5$ and $OD_5$.

Prior to implantation of the stent 10, as depicted in FIG. 1B, the third outer diameter $OD_3$, the fourth outer diameter $OD_4$, and the fifth outer diameter $OD_5$ can have similar or substantially similar sizes. And given that the outer loci of the intermediate portion 34 in the second planes extending through and along the mid-longitudinal axis MLA, the upstream portion 36, and the downstream 38 are constant or substantially constant at the maximum outer diameters $OD_3$, $OD_4$, and $OD_5$, respectively, the intermediate portion 34, the upstream portion 36, and the downstream portion 38, prior to implantation of the stent 10, have cylindrical or substantially-cylindrical shapes. Thus, prior to implantation thereof, the stent 10 is substantially cylindrical over a majority of its length, because the intermediate portion 34, the upstream portion 36, and the downstream portion 38 make up more than a majority of the length L of the stent 10. However, during and after implantation thereof, the flexibility of the stent 10 affords compressing or stretching of portions thereof, and such stretching/compressing can cause portions including the intermediate portion 34, the upstream portion 36, and the downstream portion 38 to correspondingly expand or contract. As such, portions of the intermediate portion 34, the upstream portion 36, and the downstream portion 38 will remain tubular, but will deform due to such expansion or contraction, and correspondingly, will no longer be cylindrical or substantially-cylindrical. To illustrate, when portions of the intermediate portion 34 or the downstream portion 36 are expanded or contracted, these portions can correspondingly compressed or tapered due to such expansion and contraction.

While the stent 10 (including the first waist portion 30, the second waist portion 32, the intermediate portion 34, the upstream portion 36, and the downstream portion 38) can have circular or substantially circular cross-sections in first planes perpendicular to the mid-longitudinal axis MLA, the stent 10 and the portions thereof are not so limited. All or portions of the stent 10 can have alternative shapes in the first planes perpendicular to the mid-longitudinal axis MLA, so long as such alternative shapes do not interfere with implantation of the stent 10 in the blood vessel V. When all or portions of the stent 10 have alternative shapes, these alternative shapes can have dimensions similar in size to the various diameters discussed herein.

Each of the first waist portion 30 and the second waist portion 32, as depicted in FIGS. 1A-4, are reduced-diameter portions (that resemble narrowed, pinched, or circumferentially-contracted areas) relative to remaining portions of the stent 10 that resemble generally wave-like shapes in areas along the stent 10 in the second planes extending through and along the mid-longitudinal axis MLA where the first waist portion 30 and the second waist portion 32 are located. In other areas of the stent 10 where the first waist portion 30 and the second waist portion 32 are not located (such as the upstream portion 36 and the downstream portion 38), the stent 10 can be uninterrupted by the reduced-diameter portions of the first waist portion 30 and the second waist portion 32. While the first waist portion 30 and the second waist portion 32 are provided, a multiplicity of waist portions similar to the first waist portion 30 and the second waist portion 32 may be included in alternative embodiments of the stent 10. However, as discussed below, we have found that it is preferable to position the first waist portion 30, the second waist portion 32, and such additional waist portions upstream of, but not, critically, overlapping the opening O of the aneurysm A. As discussed below, we have found, both in silico and in vitro, that positioning the additional waist portions to overlap the opening O of the aneurysm A can result in a high flow jet of blood which repeatedly strikes a point within the aneurysm A. This will weaken that point within the aneurysm and highly predispose it to rupture.

As depicted in FIG. 1A, the first waist portion 30 and the second waist portion 32 can have similar or substantially similar sizes, so that in the second planes a first maximum depth $D_1$ (at the minimum first outer diameter $OD_1$) and a second maximum depth $D_2$ (at the minimum second outer diameter $OD_2$) of the first waist portion 30 and the second waist portion 32, respectively, can have similar or substantially similar dimensions. For example, when the diameter of the blood vessel V is approximately 4 mm, the minimum first outer diameter $OD_1$ and the minimum second outer diameter $OD_2$ at the first waist portion 30 and the second waist portion 32, respectively, each can have dimensions of 3.5 mm. Furthermore, when the diameter of the blood vessel V is approximately 4 mm, the maximum third, fourth, and fifth outer diameters $OD_3$, $OD_4$, and $OD_5$ can have dimensions of 4.0 mm or approximately 4.0 mm, and correspondingly, the first maximum depth $D_1$ and the second maximum depth $D_2$ can be 0.25 mm or approximately 0.25 mm. In alternative embodiments, for example, when the maximum third, fourth, and fifth outer diameters $OD_3$, $OD_4$, and $OD_5$ have dimensions of 4.0 mm or approximately 4.0 mm, the first maximum depth $D_1$ and the second maximum depth $D_2$, for example, can range between 0.05 mm and 0.25 mm on the low side and range between 0.25 mm and 0.45 mm on the high side. And also in alternative embodiments of the stent 10, the first maximum depth $D_1$ and the second maximum depth $D_2$ could be different with the first maximum depth $D_1$ being greater than the second maximum depth $D_2$, or vice versa, and have similar ranges to those discussed above. Additionally, the first maximum depth $D_1$ and the second maximum depth $D_2$ may be proportionally adjusted according to the dimensions of the maximum third, fourth, and fifth outer diameters $OD_3$, $OD_4$, and $OD_5$. For example, if the maximum third, fourth, and fifth outer diameters $OD_3$, $OD_4$, and $OD_5$ are smaller than 4.0 mm, the first maximum depth $D_1$ and the second maximum depth $D_2$ may be proportionally smaller; and if the the maximum third, fourth, and fifth outer diameters $OD_3$, $OD_4$, and $OD_5$ are larger than 4.0 mm, the first maximum depth $D_1$ and the second maximum depth $D_2$ may be proportionally larger. Alternatively, the first maximum depth $D_1$ and the second maximum depth $D_2$ may be selected irrespective to the dimensions of the maximum third, fourth, and fifth outer diameters $OD_3$, $OD_4$, and $OD_5$ such as having the 0.25 mm depth discussed above.

Furthermore, as depicted in FIG. 1A, a distance $D_3$ between the first maximum depth $D_1$ and the second maximum depth $D_2$ could also be different between alternative embodiments of the stent 10. For example, when the diameter of the blood vessel V is approximately 4 mm and the maximum third, fourth, and fifth outer diameters $OD_3$, $OD_4$, and $OD_5$ can have dimensions of 4.0 mm or approximately 4.0 mm, the distance $D_3$ between the first maximum depth $D_1$ and the second maximum depth $D_2$ can range from 7.0 to 8.0 mm or even be larger. Furthermore, the smaller the diameter of the blood vessel V and the smaller the maximum third, fourth, and fifth outer diameters $OD_3$, $OD_4$, and $OD_5$, the distance $D_3$ can be correspondingly smaller, and the larger the diameter of the blood vessel V and the larger the maximum third, fourth, and fifth outer diameters $OD_3$, $OD_4$, and $OD_5$, the distance $D_3$ can be correspondingly larger. Varying the number of waist portions, the dimensions of the maximum depths of the waist portions, and/or the distances between the maximum depths of the waist portions can aid in deflecting portions of the blood flow BF away from the aneurysm opening O to (A) decrease the amount of blood flow BF entering the aneurysm A and (B) decrease the rate at which blood flood enters the aneurysm A, and/or (C) increase the amount and control the direction of the blood flow BF out of the aneurysm.

Furthermore, given that the outer locus of the first waist portion 30 decreases toward and then increases from the minimum first outer diameter $ID_1$, the first waist portion 30 includes an upstream substantially frusto-conical portion 40 and an oppositely-oriented downstream substantially frusto-conical portion 42; and given that the outer locus of the second waist portion 32 decreases toward and then increase from the minimum second outer diameter $ID_2$, the second waist portion 32 also includes an upstream substantially frusto-conical portion 44 and an oppositely-oriented downstream substantially frusto-conical portion 46. During and after implantation thereof, the flexibility of the stent 10 affords compressing or stretching of portions thereof, and such stretching/compressing can cause portions including the upstream substantially frusto-conical portion 40, the downstream substantially frusto-conical portion 42, the upstream substantially frusto-conical portion 44, and the downstream substantially frusto-conical portion 46 to correspondingly expand or contract and cause deformation thereof. However, during such expansion and contraction, the upstream substantially frusto-conical portion 40, the downstream substantially frusto-conical portion 42, the upstream substantially frusto-conical portion 44, and the downstream substantially frusto-conical portion 46 will remain substantially frusto-conical.

As depicted in FIGS. 1A and 1B, the upstream substantially frusto-conical portion 40 and the downstream substantially frusto-conical portion 42 (of the first waist portion 30) have similar, but oppositely-oriented slopes in the second planes extending through and along the mid-longitudinal axis MLA; and the upstream substantially frusto-conical portion 44 and the downstream substantially frusto-conical portion 46 (of the second waist portion 32) have similar, but oppositely-oriented slopes in the in the second planes extending through and along the mid-longitudinal axis MLA. However, the slopes of portions of the first waist portion 30, the second waist portion 32, and any additional waist portions in the second planes are not so limited. For example, the slopes of portions of the first waist portion 30 and the second waist portion 32 in the second planes on opposite sides of the first planes perpendicular to the mid-longitudinal axis MLA extending through the minimum first outer diameter $OD_1$ and the minimum second outer diameter $OD_2$ can have similar or different constant or varied slopes having correspondingly similar or different gradual or steeper angles. As such, the portions of the first waist portion 30 and the second waist portion 32 in the second planes on opposite sides of the first planes can have symmetrical or asymmetrical configurations about the first planes extending through the minimum first outer diameter $OD_1$ and the minimum second outer diameter $OD_2$. The additional waist portions can also have similar symmetrical or asymmetrical configurations.

Because of cross-sections of the strands of material of the first coil $C_1$ and the second coil $C_2$ in planes extending through the mid-longitudinal axis MLA are uniform in FIGS. 1A and 2-4, the inner loci of the first waist portion 30, the second waist portion 32, the intermediate portion 34, the upstream portion 36, and the downstream portion 38 have shapes corresponding to the shapes of the outer loci thereof. Alternatively, as discussed below, the cross-sections of the strands of material of the first coil $C_1$ and the second coil $C_2$ in the planes extending through the mid-longitudinal axis MLA, and thus, the outer loci and the inner loci can vary rather than correspond to one another.

Figure 5:
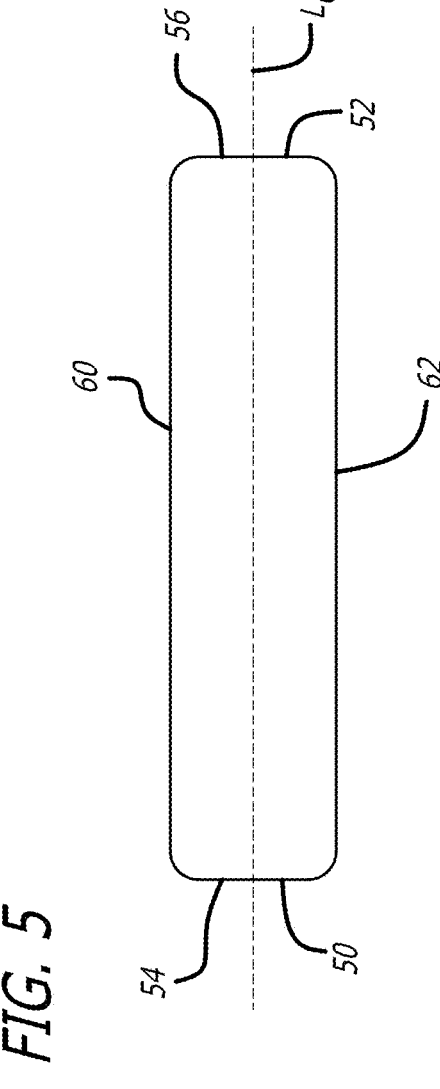
FIG. 5 is a cross-sectional view of a portion of a strand of material forming a coil of the stent of FIG. 1A.
Figure 6A:
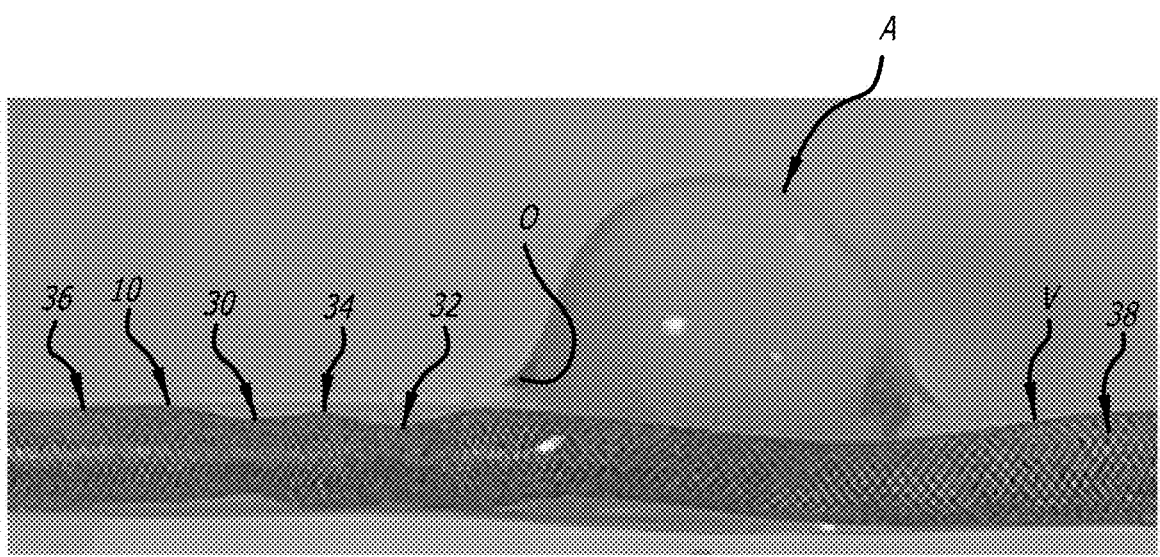
FIGS. 6(A)-(G) are successive snap-shots of a video of a test rig simulating blood flow through a blood vessel and an aneurysm as effected by placement of the stent of FIG. 1.
Figure 6B:
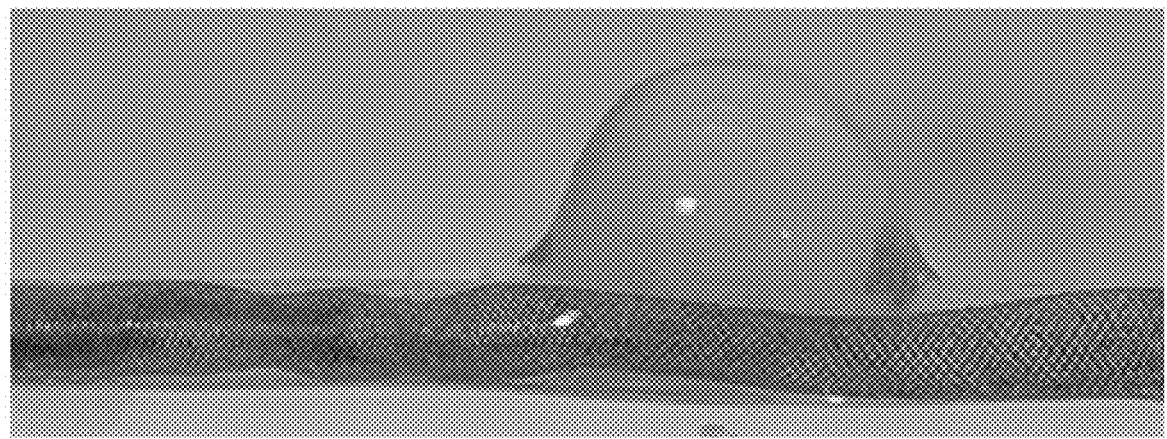
Figure 6C:
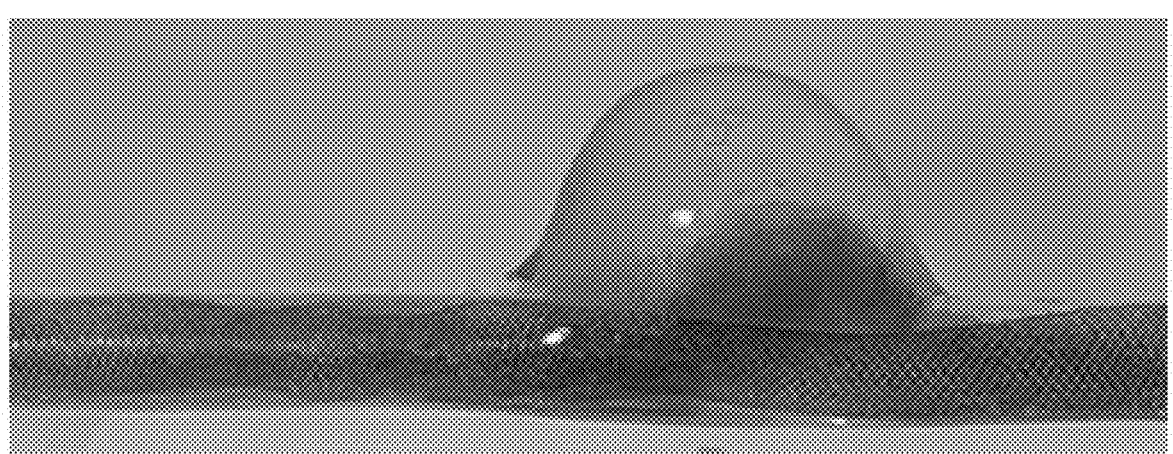
Figure 6D:
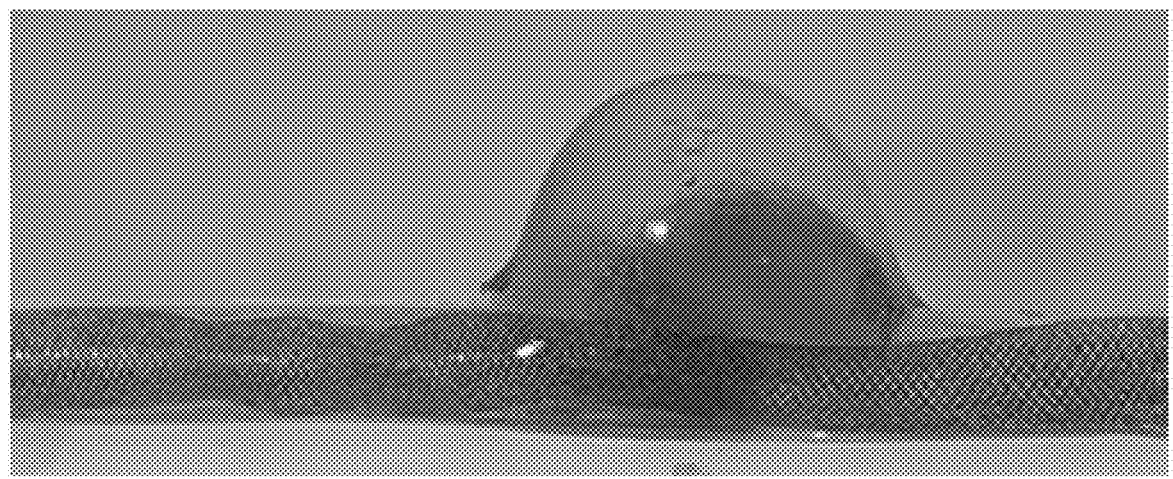
Figure 6E:
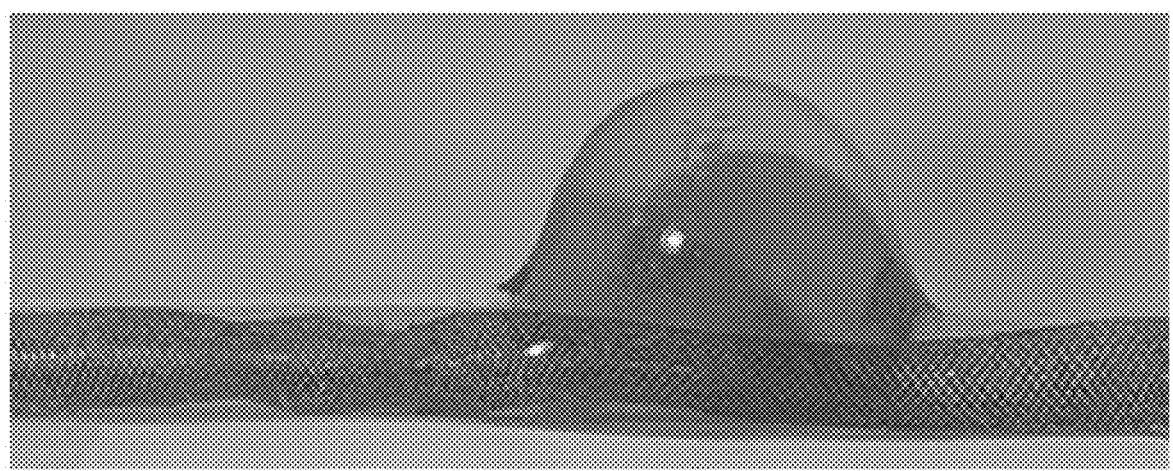
Figure 6F:
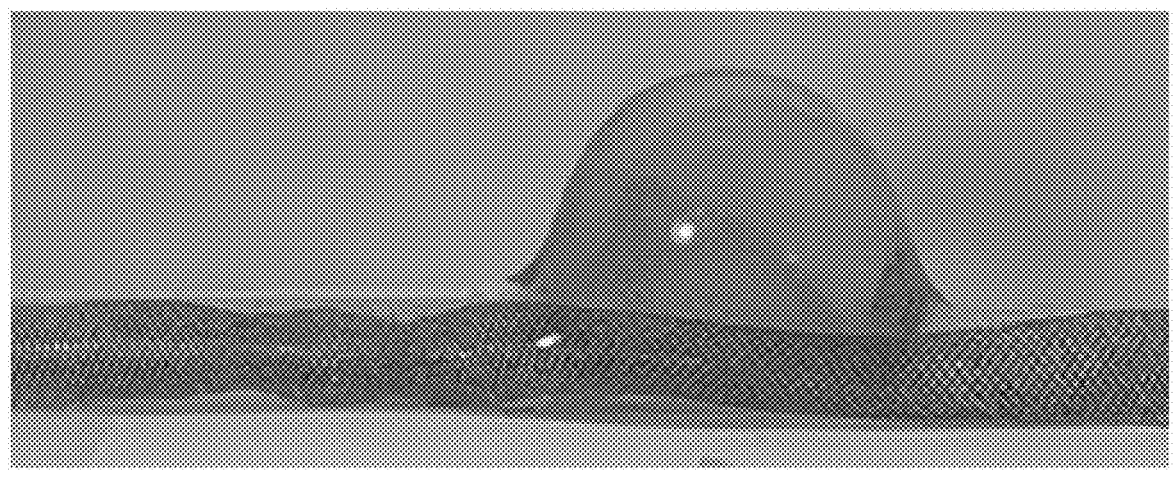
Figure 6G:
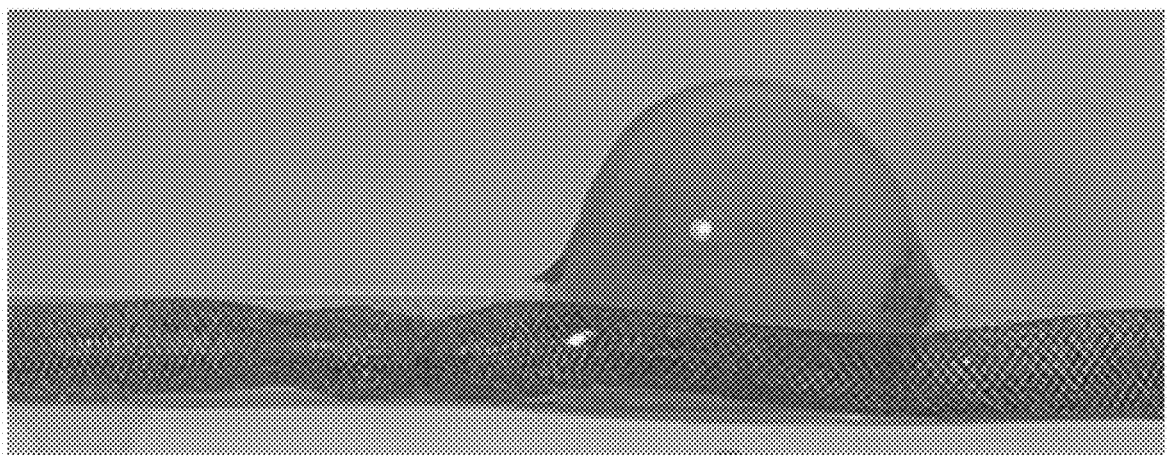
Figure 7A:
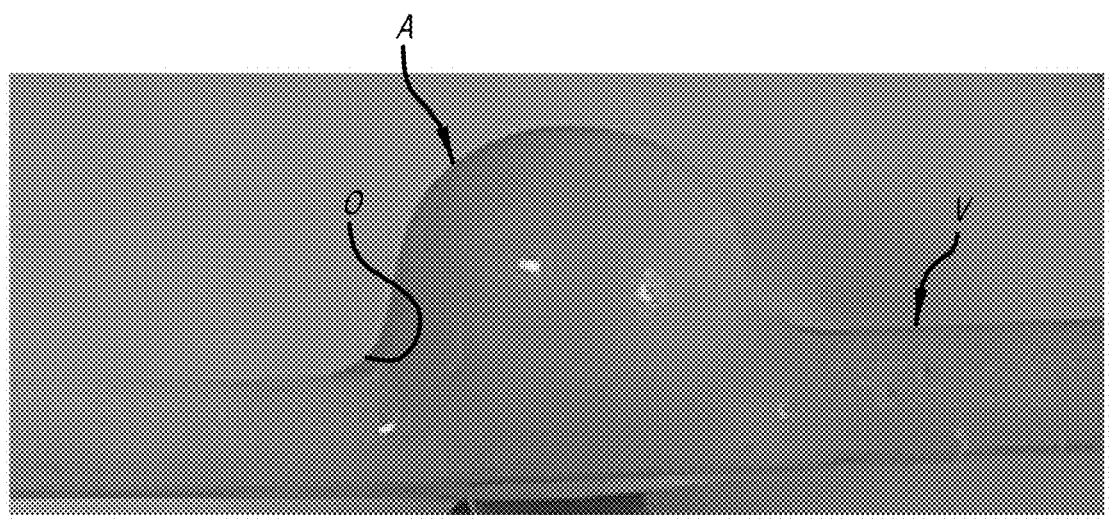
FIGS. 7(A)-(D) are successive snap-shots of a video of a test rig simulating blood flow through a blood vessel and an aneurysm without presence of the stent of FIG. 1.
Figure 7B:
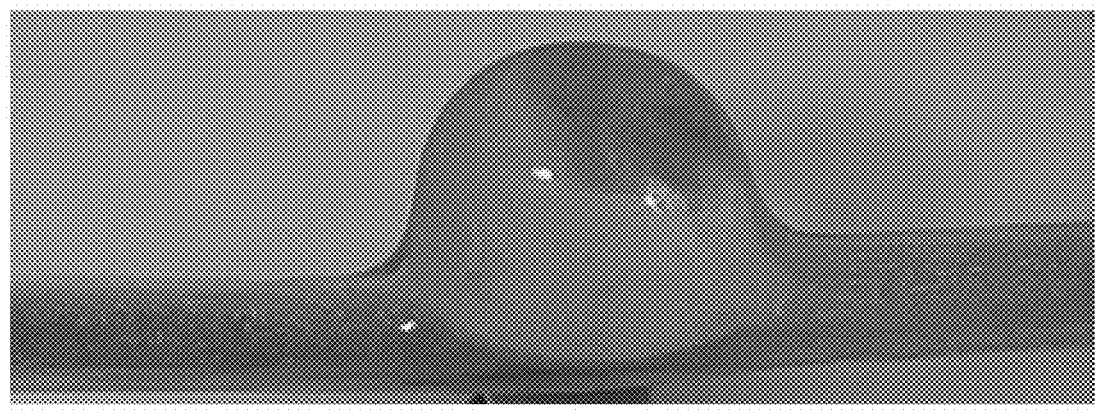
Figure 7C:
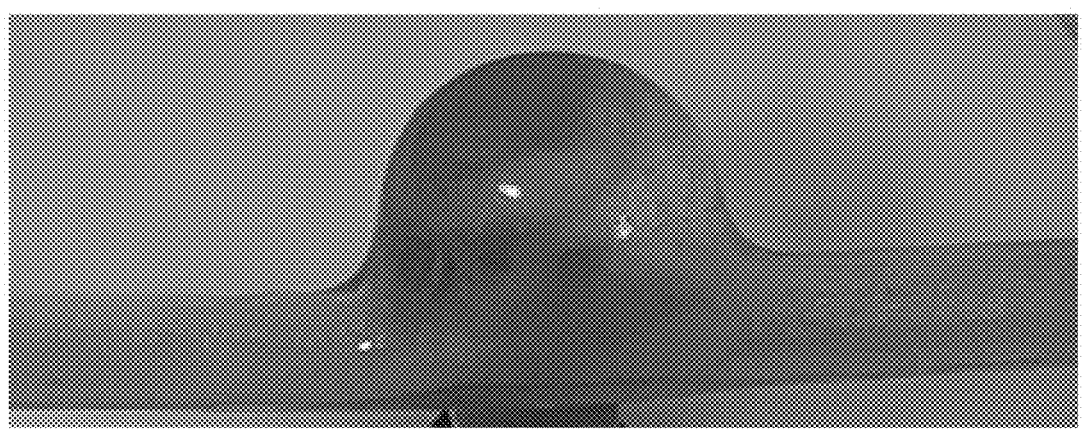
Figure 7D:
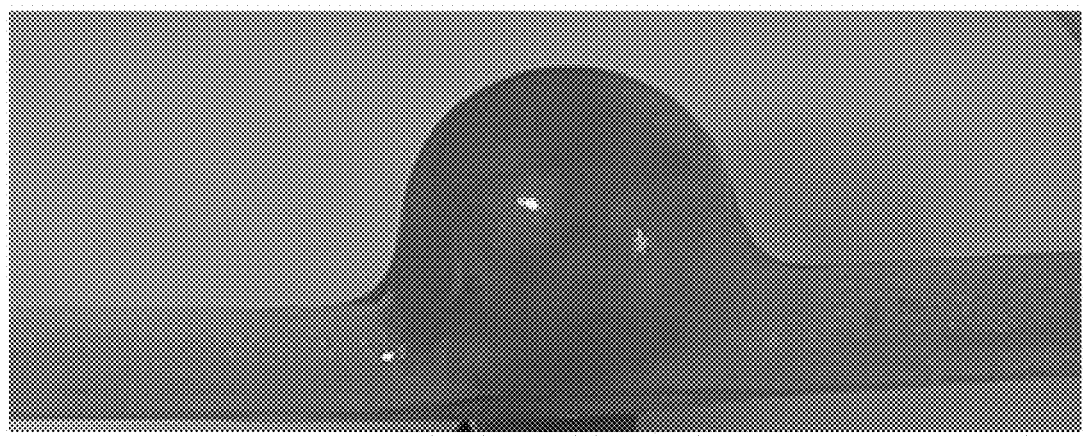

The wire strands of material forming the first coil $C_1$ and the second coil $C_2$ of the stent 10 could have various cross-sectional shapes in the second planes extending through and along the mid-longitudinal axis MLA. For example, the wire strand of material could have, for example, fully or partially flattened, arcuate, circular, oval, elliptical, or wing-shaped cross-sectional shapes. These cross-sections can be uniform or vary along the length L of the stent 10. When the cross-sections of the strand of material vary along the length L of the stent 10, these cross-sections can include these various cross-sectional shapes and various transitions therebetween. Each of these cross-sectional shapes can have a leading end, a trailing end, a leading end surface, a trailing end surface, an outer surface, and an inner surface. As depicted in FIG. 5, an exemplary cross-section of the strands forming the first coil C₁ and the second coil C₂ in the second plane extending through and along the mid-longitudinal axis MLA has a flattened shape, and includes a leading end 50, a trailing end 52, a leading end surface 54, a trailing end surface 56, an outer surface 60, and an inner surface 62. The outer surfaces 60 in the second planes extending through and along the mid-longitudinal axis MLA form at least part of the exterior facing surfaces 20, and the inner surfaces 62 in the second planes extending through and along the mid-longitudinal axis MLA form at least part of the interior facing surfaces 22.

Each of the cross-sectional shapes of the strands forming the first coil C₁ and the second coil C₂ including the exemplary flattened shape (FIG. 5) can include an axis $L_C$ extending through the leading end 50 and the trailing end 52. Furthermore, when the cross-sectional shape of the strand material is fully or partially flattened, oval, elliptical, or wing-shaped, the axis $L_C$ would be a longitudinal axis of the corresponding cross-sectional shape. A circular cross-sectional shape would, of course, not have a longitudinal axis. Orientation of the axis $L_C$ can be varied relative to the blood flow. To illustrate, the axis $L_C$ can be aligned with, oriented at an acute angle, or oriented at an obtuse angle with respect to the blood flow. The orientations of the $L_C$ can determine the amount of contact of the blood flow with either the outer surfaces 60 or the inner surfaces 62, and such contact can aid in deflecting portions of the blood flow BF away from the aneurysm opening O to (A) decrease the amount of blood flow BF entering the aneurysm A and (B) decrease the rate at which blood flood enters the aneurysm A, and/or (C) increase the amount and control the direction of the blood flow BF out of the aneurysm.

The interior passage 24 can receive a guidewire (not shown) therethrough to facilitate, for example, placement of the stent 10 in the blood vessel V adjacent the aneurysm A. As depicted in FIGS. 2-4, the stent 10 can be positioned in the blood vessel V such that both of the first waist portion 30 and the second waist portion 32 are positioned upstream, and the second waist portion 32 is positioned just or immediately upstream of the opening O of the aneurysm A. After implantation of the stent 10 in the blood vessel V, most of the blood flow BF primarily will be shunted through the interior passage 24 and contact the interior-facing surfaces 22 (and the inner surfaces 62 of the cross-sectional shapes of the strands) in a direction from the first end 12 to the second end 14 of the stent 10. Also, after implantation of the stent 10 in the blood vessel V, some of the blood flow BF will flow over the exterior-facing surfaces 20 (and the outer surfaces 60 of the cross-sectional shapes of the strands) in the direction from the first end 12 to the second end 14 of the stent 10, and some of the blood flow BF will pass through the uniform first spaces S₁, the varied second spaces S₂, and the uniform third spaces S₃ between the windings of the first coil C₁ and the second coil C₂ from the interior passage 24 to the exterior to the stent 10. More of the blood flood BF will pass through the larger third spaces S₃, than the smaller first spaces S₁ and second spaces S₂. The first spaces S₁, the second spaces S₂, and the third spaces S₃, the sizes thereof, and the amount of blood flow BF passing therethrough can aid in deflecting portions of the blood flow BF away from the aneurysm opening O to (A) decrease the amount of blood flow BF entering the aneurysm A and (B) decrease the rate at which blood flood enters the aneurysm A, and/or (C) increase the amount and control the direction of the blood flow BF out of the aneurysm.

Furthermore, positioning of the first waist portion 30 and the second waist portion 32 upstream of the opening O of the aneurysm A with the second waist portion 32 positioned just or immediately upstream of the opening O of the aneurysm A allows the blood flow BF to interact with the first waist portion 30 and the second waist portion 32 before reaching the opening O of the aneurysm A both at the interior-facing surfaces 22 (and the inner surfaces 62 of the cross-sectional shapes of the strands) and the exterior-facing surfaces 20 (and the outer surfaces 60 of the cross-sectional shapes of the strands). Computer modeling (FIG. 4) and modeling using a test rig (FIGS. 6(A)-(G)) of the blood flow BF through the stent 10 and the blood vessel V has revealed that the configuration and positioning of the first waist portion 30 and the second waist portion 32 relative to the opening O of the aneurysm A and the interaction of the blood flow BF therewith can advantageously maximize the blood flow BF away from and out of the aneurysm A. The configuration and placement of the stent 10 relative the opening O and the interaction of the blood flow BP therewith can serve to deflect portions of the blood flow BF away from the aneurysm opening O to (A) decrease the amount of blood flow BF entering the aneurysm A and (B) decrease the rate at which blood flood enters the aneurysm A, and/or (C) increase the amount and control the direction of the blood flow BF out of the aneurysm A.

A preferred embodiment of the stent 10 includes two (2) waist portions such as the first waist portion 30 and the second waist portion 32 that are positioned in the blood vessel V before the opening O to the aneurysm A, as depicted in FIGS. 2-4 and 6(A)-6(G). Using the computer modeling and the test rig, we have discovered that using two waist portions immediately upstream of the opening O provides superior results for advantageously decreasing the amount of blood flow BF entering the aneurysm A, and advantageously increasing the amount and controlling the direction of the blood flow BF out of the aneurysm A. For example, use of the two (2) waist portions, along with the orientation of the axes $L_C$ of the cross-sectional shapes of the first coil C₁ and the second coil C₂, can control the direction of the blood flow BF upstream of the aneurysm A to advantageously affect the amount of blood flow entering the aneurysm A and advantageously affect the amount and direction of blood flow BF out of the aneurysm A.

To illustrate, as depicted in FIG. 4, we have found, in silico, via the computer modeling that the configuration of the stent 10 adjacent the two (2) waist portions and the orientation of the axes $L_C$, with the two (2) waist portions positioned upstream of the opening O, direct the blood flow upwardly and then downwardly across the space of the blood vessel V at the first waist portion 30 and the second waist portion 32. The configuration of the stent adjacent the two (2) waist portions and the orientation of the axes $L_C$ thereby produces a pressure wave pattern and/or ripple effect in the blood flow BF that advantageously affects the same. Such upward and then downward direction of the blood flow BF can advantageously maximize the blood flow BF away from and out of the aneurysm A by (A) decreasing the amount of the blood flow BF entering the aneurysm A, and critically, (B) decreasing the rate at which the blood flow enters the aneurysm, and/or also (C) increasing the amount and controlling the direction of the blood flow BF out of the aneurysm A. We have also found, in silico, via the computer modeling that positioning additional waist portions to overlap the opening O of the aneurysm A can result in highly unfavorable additional blood flow through the opening O and into the aneurysm A.

Furthermore, as depicted in FIGS. 6(A)-(G), the test rig reveals that the configuration of the stent 10 adjacent the two (2) waist portions, with the two (2) waist portions positioned upstream of the opening O, limits the amount of blood flowing through the opening O into the aneurysm A, and critically, limits the rate at which blood flows through the opening O into the aneurysm A. The test rig used in FIGS. 6(A)-(G) is formed by a viscoelastic tube expanded to simulate an artery and the aneurysm A, and uses transparent non-Newtonian fluid pumped in a pulsatile manner therethrough to simulate a heart pumping blood through the blood vessel V. Colored dye, as depicted in FIGS. 6(A)-(G), is added to the transparent non-Newtonian fluid to simulate flow of the blood through the test rig, and the simulation demonstrates at least that both the amounts of the colored dye that flow through the opening O into the aneurysm A, and the rate at which the colored dye flows through the opening O into the aneurysm A are both comparably limited. Such limited amounts of the colored dye that flow though the opening O into the aneurysm A and the limited rate at which the colored dye flows through the opening O into the aneurysm A when the stent 10 is used can be contrasted with FIGS. 7(A)-(D) where colored dye flows freely into and swirls within the aneurysm A. FIGS. 7(A)-(D) depicts a similarly-constructed test rig formed by a viscoelastic tube expanded to simulate an artery and the aneurysm A that uses the transparent non-Newtonian fluid (with the colored dye added thereto) pumped in a pulsatile manner therethrough to simulate a heart pumping blood through the blood vessel V without use of the stent 10. Additionally, we have found, in vitro, via use of the test rig that positioning additional waist portions to overlap the opening O of the aneurysm A again can result in highly unfavorable additional blood flow through the opening O and into the aneurysm A.

From the computer modeling (in silico) and the test rig (in vitro), we have found that adding a multiplicity of additional waists upstream of the opening O does not markedly improve the results afforded by the stent 10, adding a multiplicity of additional waists downstream of the opening O does not improve the results afforded by the stent 10, and having either of the two waist portions or any additional waists overlap the opening O of the aneurysm A (i.e., opposite from and/or under/over the opening O in areas of the blood vessel V between the upstream areas and downstream portion areas of the blood vessel V relative to the opening O) actually markedly decreases the results in comparison to the preferred stent described herein, and can result in highly unfavorable additional blood flow through the opening O and into the aneurysm A. Furthermore, it is also advantageous to maximize the interior dimensions of the stent 10 over the length L thereof to limit choke points in the interior passage 24 to inhibit potential formation of blood clots while simultaneously maintaining blood flow. Thus, use of two (2) waist portions (such as the first waist portion 30 and the second waist portion 32), as evidenced by the computer modeling and the test rig, provides the above-discussed advantageous results, while inhibiting blood clot formation.

As previously described, a preferred first waist portion 30 and second waist portion 32 are positioned upstream of the opening O to the aneurysm A, while the tubular downstream portion 38 is uninterrupted adjacent the opening O to the aneurysm A and immediately downstream of the opening O to the aneurysm A by additional waists. A preferred stent 10 need be of sufficient length to provide at least two waists upstream of the opening O to the aneurysm A with sufficient spacing between the two waists, an uninterrupted tubular downstream portion 38 adjacent to adjacent the opening O to the aneurysm A and immediately downstream of the opening O to the aneurysm A, and sufficient length downstream of the aneurysm opening to be stable within the blood vessel V. The aneurysm openings to be treated cover a wide range of conditions and sizes, therefore necessitating a considerable range of stent length options. By way of example, aneurysm openings may be one millimeter or smaller to 25 millimeters or even larger. The downstream tubular portion 38 of a preferred stent 10 adjacent the opening O to the aneurysm A and immediately downstream of the opening O to the aneurysm A will have no additional waists along this portion of the length of the stent 10.

The first waist portion 30 and second waist portion 32 in a preferred embodiment of the stent 10 are both located along the length of the stent 10 in the first 50% as measured from the upstream first end 12 of the stent 10. In alternative embodiments of the stent 10, the first waist portion 30 and second waist portion 30 may be located along, for example, the first 55%, 60%, 65% or 70% as measured from the upstream first end 12 of the stent 10. While in certain embodiments of the stent 10 more than two waists may be positioned upstream of the opening O to the aneurysm A, a preferred embodiment of the stent 10 only includes two waists positioned upstream of the opening O to the aneurysm A. And more preferably, this embodiment of the stent 10 only includes two waists along the entire length of the stent 10. For embodiments of the stent 10 having one or more waists downstream of the opening O to the aneurysm A, a preferred embodiment of the stent 10 includes downstream waists having a larger or a smaller minimum diameter than the minimum diameters of the first waist portion 30 and second waist portion 32 positioned upstream of the opening O to the aneurysm A. Another preferred embodiment of the stent 10 has no waists either adjacent to the opening O to the aneurysm A or downstream of the opening O to the aneurysm. These embodiments of the stent 10 will thus have no waists, for example, on the downstream most half of the stent, or the downstream most 60% of the length of the stent, or the downstream most 70% of the length of the stent, or the downstream most 80% of the length of the stent.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with the stent 10 and the methods for use of the stent 10.

We claim:

1. A method for optimal placement of a stent in a blood vessel adjacent an opening to an aneurysm and using the stent to reduce deleterious effects of blood flow on the aneurysm, the method comprising:

providing the stent having a tubular shape and being formed by a first helical coil and a second helical coil interwoven with one another, the stent having a first end, an opposite second end, a length extending between the first end and the second end, an exterior surface extending along the length, a mid-longitudinal axis extending through the first end and the second end, a first opening at the first end, a second opening at the second end, and an interior passageway extending between the first opening and the second opening;

implanting the stent in the blood vessel by positioning portions of the tubular shape of the stent upstream and downstream of the opening to the aneurysm, positioning a first waist and a second waist formed in the tubular shape of the stent upstream of the opening to the aneurysm, and contacting the exterior surface of the stent with a wall of the blood vessel adjacent the opening to the aneurysm, a multitude of spaces between the windings of the first helical coil and the second helical coil being formed in the tubular shape along the length of the stent with the multitude of spaces positioned across the opening to the aneurysm being larger than the multitude of spaces positioned upstream of the opening to the aneurysm, the first waist and the second waist being formed as narrowed areas in the exterior surface of the tubular shape, the first waist and the second waist being positioned adjacent to another, the second waist being closer to the second end than the first waist, and the first waist and the second waist each having minimum outer diameters smaller than maximum outer diameters of the tubular shape adjacent the first waist and the second waist in corresponding planes extending therethrough that are perpendicular to the mid-longitudinal axis;

forming, during the implanting of the stent in the blood vessel, a first void and a second void between the stent and portions of the blood vessel in areas between the first waist and the wall, and between the second waist and the wall, respectively;

after the implanting of the stent in the blood vessel, directing flow of blood through the blood vessel by directing first portions of the flow of the blood through the passageway, and directing second portions of the flow of blood through the passageway, from the passageway out of the multitude of spaces in a first upstream portion of the second waist adjacent the second void and into the second void, across the second void, into the multitude of spaces in a first downstream portion of the second waist adjacent the second void and out of the second void, and back into the passageway; and after the implanting of the stent in the blood vessel, generating a pressure wave and/or ripple effect in the flow of blood via interaction of the second portions of the flow of blood with the multitude of spaces in the first upstream portion of the second waist, the second void, and the multitude of spaces in the first downstream portion of the second waist to direct the flow of blood away from the aneurysm, and increase the amount and control the direction of the flow of blood out of the aneurysm;

wherein the forming of the first void and the second void, and interaction of the second portions of the flow of blood with the second void affords movement of the second portions of the flow of blood out of and back into the passageway of the stent via the multitude of spaces;

wherein, when the first waist and the second waist are positioned upstream of the opening to the aneurysm, the tubular shape is uninterrupted adjacent the opening to the aneurysm and immediately downstream of the opening to the aneurysm by additional waists.

2. The method of claim 1, further comprising decreasing amounts of flow of blood into aneurysm via the interaction of the flow of blood with the multitude of spaces in the first upstream portion of the second waist, the second void, and the multitude of spaces in the first downstream portion of the second waist.

3. The method of claim 1, wherein the first upstream portion of the second waist is upstream of the minimum outer diameter thereof and the first downstream portion of the second waist is downstream of the minimum outer diameter thereof, the first waist includes a second upstream portion upstream of the minimum outer diameter thereof and a second downstream portion downstream of the minimum outer diameter thereof, and opposed ones of the first upstream portion, the second upstream portion, the first downstream portion, and the second downstream portion of the first waist and the second waist can have similar or different constant or varied slopes and correspondingly symmetrical or asymmetrical configurations in a first plane extending through and along the mid-longitudinal axis.

4. The method of claim 3, wherein the first upstream portion and the second downstream portion of the second waist are substantially frusto-conical, and the second upstream portion and the second downstream portion of the first waist are substantially frusto-conical.

5. The method of claim 1, wherein the minimum outer diameter of the first waist is in a first plane perpendicular to the mid-longitudinal axis, and the minimum outer diameter of the second waist is in a second plane perpendicular to the mid-longitudinal axis, and, in third planes perpendicular to the mid-longitudinal axis, upstream portions of the first waist and the second waist include diameters that decrease toward the minimum outer diameters thereof, and downstream portions of the first waist and the second waist include diameters that increase from the minimum outer diameters thereof.

6. The method of claim 5, wherein an intermediate portion is positioned between the first waist and the second waist, the intermediate portion having a maximum dimension in a fourth plane perpendicular to the mid-longitudinal axis approximately identical to maximum diameters of upstream portions and downstream portions of the stent in fifth planes and sixth planes, respectively, perpendicular to the mid-longitudinal axis.

7. The method of claim 1, wherein the first void and the second void are uninterrupted by portions of the stent and the wall of the blood vessel.

8. The method of claim 1, wherein the passageway includes an interior surface, and wherein the first waist and the second waist each have shapes along the interior surface of the interior passageway corresponding to shapes thereof on the exterior surface of the stent.

9. The method of claim 1, further comprising, after the implanting of the stent in the blood vessel and prior to the interaction of the second portions of the flow of blood with the second void, directing the second portions of the flow of blood through the passageway, from the passageway out of the multitude of spaces in a second upstream portion of the first waist adjacent the first void and into the first void, across the first void, into the multitude of spaces in a second downstream portion of the first waist adjacent the first void and out of the first void, and back into the passageway.

10. The method of claim 9, wherein interaction of the second portions of the flow of blood with the first void affords movement of the second portions of the flow of blood out of and back into the passageway of the stent via the multitude of spaces.

11. A method for optimal placement of a stent in a blood vessel adjacent an opening to an aneurysm and using the stent to reduce deleterious effects of blood flow on the aneurysm, the method comprising:

implanting the stent in the blood vessel by positioning portions of a tubular shape of the stent upstream and downstream of the opening to the aneurysm, positioning a first waist and a second waist formed in the tubular shape of the stent upstream of the opening to the aneurysm, and contacting exterior surfaces of the stent with a wall of the blood vessel adjacent the opening to the aneurysm, the tubular shape of the stent being formed by interwoven windings of a first helical coil and a second helical coil, a multitude of spaces being formed in the stent between the first helical coil and the second helical coil along a length of the stent with the multitude of spaces positioned across the opening to the aneurysm being larger than the multitude of spaces positioned upstream of the opening to the aneurysm, an interior passageway being formed through the tubular shape of the stent, the first waist and the second waist being formed as narrowed areas in the exterior of the tubular shape, the first waist and the second waist being positioned adjacent to another, the first waist and the second waist each having minimum outer diameters smaller than maximum outer diameters of the tubular shape adjacent the first waist and the second waist in corresponding planes extending therethrough that are perpendicular to a mid-longitudinal axis of the stent;

forming, during the implanting of the stent in the blood vessel, a first void and a second void between the stent and portions of the blood vessel in areas between the first waist and the wall, and between the second waist and the wall, respectively;

after the implanting of the stent in the blood vessel, directing flow of blood through the blood vessel by directing first portions of the flow of the blood through the passageway, and directing second portions of the flow of blood through the passageway, from the passageway out of the multitude of spaces in a first upstream portion of the second waist adjacent the second void and into the second void, across the second void, into the multitude of spaces in a first downstream portion of the second waist adjacent the second void and out of the second void, and back into the passageway; and after the implanting of the stent in the blood vessel, generating a pressure wave and/or ripple effect in the flow of blood via interaction of the second portions of the flow of blood with the multitude of spaces in the first upstream portion of the second waist, the second void, and the multitude of spaces in the first downstream portion of the second waist to direct the flow of blood away from the aneurysm, and increase the amount and control the direction of the flow of blood out of the aneurysm;

wherein the forming of the first void and the second void, and interaction of the second portions of the flow of blood with the second void affords movement of the second portions of the flow of blood out of and back into the passageway of the stent via the multitude of spaces;

wherein, when the first waist and the second waist are positioned upstream of the opening to the aneurysm, the tubular shape is uninterrupted adjacent the opening to the aneurysm and immediately downstream of the opening to the aneurysm by additional waists.

12. The method of claim 11, further comprising decreasing amounts of flow of blood into the aneurysm via the interaction of the flow of blood with the multitude of spaces in the first upstream portion of the second waist, the second void, and the multitude of spaces in the first downstream of the second waist.

13. The method of claim 11, wherein the first upstream portion of the second waist is upstream of the minimum outer diameter thereof and the first downstream portion of the second waist is downstream of the minimum outer diameter thereof, the first waist includes a second upstream portion upstream of the minimum outer diameter thereof and a second downstream portion downstream of the minimum outer diameter thereof, and opposed ones of the first upstream portion, the second upstream portion, the first downstream portion, and the second downstream portion of the first waist and the second waist can have similar or different constant or varied slopes and correspondingly symmetrical or asymmetrical configurations in a first plane extending through and along the mid-longitudinal axis.

14. The method of claim 13, wherein the first upstream portion and the first downstream portion of the second waist are substantially frusto-conical, and the second upstream portion and the second downstream portion of the first waist are substantially frusto-conical.

15. The method of claim 11, wherein the minimum outer diameter of the first waist is in a first plane perpendicular to the mid-longitudinal axis, and the minimum outer diameter of the second waist is in a second plane perpendicular to the mid-longitudinal axis, and, in third planes perpendicular to the mid-longitudinal axis, upstream portions of the first waist and the second waist include diameters that decrease toward the minimum outer diameters thereof, and downstream portions of the first waist and the second waist include diameters that increase from the minimum outer diameters thereof.

16. The method of claim 11, wherein the first void and the second void are uninterrupted by portions of the stent and the wall of the blood vessel.

17. The method of claim 11, wherein first waist and the second waist each have shapes along the interior passageway corresponding to shapes thereof on the exterior of the stent.

18. The method of claim 11, further comprising, after the implanting of the stent in the blood vessel and prior to the interaction of the second portions of the flow of blood with the second void, directing the second portions of the flow of blood through the passageway, from the passageway out of the multitude of spaces in a second upstream portion of the first waist adjacent the first void and into the first void, across the first void, into the multitude of spaces in a second downstream portion of the first waist adjacent the first void and out of the first void, and back into the passageway.

19. The method of claim 18, wherein interaction of the second portions of the flow of blood with the first void affords movement of the second portions of the flow of blood out of and back into the passageway of the stent via the multitude of spaces.

* * * * *